United States Patent [19]

Heiker et al.

[11] Patent Number: 5,721,238
[45] Date of Patent: Feb. 24, 1998

[54] 2,8-DISUBSTITUTED QUINAZOLINONES

[75] Inventors: Fred Robert Heiker, Wuppertal; Ulrich Niewöhner, Wermelskirchen, both of Germany; Wolfgang Hartwig, Stamford, Conn.; Helmuth Schütz, Wuppertal, Germany; Erwin Bischoff, Wuppertal, Germany; Elisabeth Perzborn, Wuppertal, Germany; Matthias Schramm, Leverkusen, Germany

[73] Assignee: Bayer Aktiengesellschaft, Leverkusen, Germany

[21] Appl. No.: 584,865

[22] Filed: Jan. 11, 1996

[30] Foreign Application Priority Data

Jan. 19, 1995 [DE] Germany ............ 195 01 481.2

[51] Int. Cl.⁶ .................. A61K 31/505; C07D 239/80
[52] U.S. Cl. ............................ 514/259; 544/289
[58] Field of Search ..................... 544/289; 514/259

[56] References Cited

U.S. PATENT DOCUMENTS

| | | | |
|---|---|---|---|
| 3,169,129 | 2/1965 | Rodgers et al. | 260/251 |
| 4,431,440 | 2/1984 | Bhalla et al. | 71/92 |
| 5,294,612 | 3/1994 | Bacon et al. | 514/234.2 |
| 5,482,941 | 1/1996 | Terrett | 514/253 |

FOREIGN PATENT DOCUMENTS 9312095  6/1993  WIPO.

OTHER PUBLICATIONS

S. Takano, et al., Heterocycles, vol. 29, No. 2, pp. 249–252, (1989).

M. Hoey, et al., Biochem. Pharmacol., vol. 40, pp. 193–202, (1990).

Primary Examiner—Matthew V. Grumbling
Attorney, Agent, or Firm—Sprung Kramer Schaeffer & Briscoe

[57] ABSTRACT 2,8-Disubstituted quinazolinones are prepared by first subjecting the quinazolinone basic skeleton to condensation by customary reactions and then introducing the desired substituents into the 8-position. The compounds are suitable as active compounds in medicaments, in particular for the treatment of inflammations, thromboembolic diseases and cardiovascular diseases.

16 Claims, No Drawings

2,8-DISUBSTITUTED QUINAZOLINONES

The present invention relates to 2,8-disubstituted quinazolinones, a process for their preparation and their use in medicaments, in particular for the treatment of inflammations, thromboembolic and cardiovascular diseases and diseases of the urogenital system.

Quinazolinones having a selective cGMP PDE-inhibitory action are known from the publication PCT WO 93/12095.

Phosphodiesterases (PDEs) play an essential role in the regulation of the intracellular cGMP and cAMP level. The phosphodiesterase isoenzyme groups PDE I to PDE V described to date [nomenclature according to Beavo and Reifsnyder (cf. Beavo, J. A. and Reifsnyder, D. H.: Trends in Pharmacol. Sci. 11, 150–155 (1990))], the Ca-calmodulin-activated PDE I, the cGMP-stimulatable PDE II and the cGMP-specific PDE V are essentially responsible for the metabolism of cGMP. Because of the different distribution of these cGMP-metabolizing PDEs in tissue, selective inhibitors should raise the cGMP level in the corresponding tissue according to the distribution of the corresponding isoenzyme in the tissue. This can lead to a specific, antiaggregatory, antispastic, vasodilating, antiarrhythmic and/or antiinflammatory action.

The present invention thus relates to 2,8-disubstituted quinazolinones of the general formula (I)

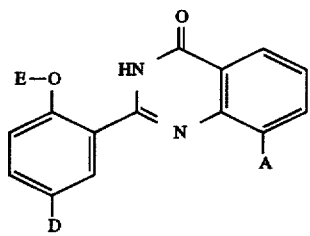

in which

A represents oxiranyl, which is optionally substituted by straight-chain or branched alkyl having up to 8 carbon atoms, which in turn can be substituted by phenyl, or represents a radical of the formula

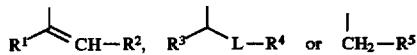

wherein

R denotes hydrogen or straight-chain or branched alkyl having up to 6 carbon atoms, $R^2$ denotes straight-chain or branched alkyl having up to 8 carbon atoms, which is optionally substituted by phenyl, $R^3$ denotes straight-chain or branched alkyl having up to 5 carbon atoms or a group of the formula —$OR^6$,
wherein $R^6$ denotes hydrogen, a hydroxyl-protecting group or straight-chain or branched alkyl having up to 5 carbon atoms, $R^4$ denotes straight-chain or branched alkyl having 2 to 10 carbon atoms, which is optionally substituted by phenyl, L denotes a radical of the formula —CO—, —CH(OH), —$CH_2$, —$CH(N_3)$ or —$CH(OSO_2R^7)$,
wherein $R^7$ denotes straight-chain or branched alkyl having up to 4 carbon atoms or phenyl, $R^5$ denotes straight-chain or branched alkyl having 3 to 8 carbon atoms, which is optionally substituted by phenyl, or denotes benzyl or 2-phenylethyl, D represents hydrogen, or represents a group of the formula —$SO_2$—$NR^8R^9$,
wherein $R^8$ and $R^9$ are identical or different and denote hydrogen, phenyl or straight-chain or branched alkyl having up to 6 carbon atoms, which is optionally substituted by hydroxyl, or, together with the nitrogen atom, form a 5- to 6-membered saturated heterocyclic radical which has up to 2 further hetero atoms from the series consisting of S, N and/or O and is optionally substituted, including via a free N function, by straight-chain or branched alkyl having up to 6 carbon atoms, which in turn can be substituted by hydroxyl, and E represents straight-chain or branched alkyl having up to 8 carbon atoms, and tautomers and salts thereof.

The substances according to the invention can also be in the form of salts. Physiologically acceptable salts are preferred in the context of the invention.

Physiologically acceptable salts can be salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds of the general formula (I) according to the invention can occur in various stereochemical forms which either behave as mirror images (enantiomers) or do not behave as mirror images (diastereomers). The invention relates both to the antipodes and to the racemic forms as well as the diastereomer mixtures. The racemic forms, like the diastereomers, can be separated into the stereoisomerically uniform constituents in a known manner.

A 5- to 6-membered saturated heterocyclic radical which is bonded via the nitrogen atom and can furthermore contain up to 2 oxygen, sulphur and/or nitrogen atoms as heteroatoms in general represents piperidyl, morpholinyl or piperazinyl. Morpholinyl is particularly preferred.

Hydroxyl-protecting group in the context of the above-mentioned definition in general represents a protective group from the series consisting of trimethylsilyl, triethylsilyl, triisopropylsilyl, tert-butyl-dimethylsilyl, triphenylsilyl or benzyl. Trimethylsilyl, tert-butyl-dimethylsilyl or benzyl are preferred.

Preferred compounds are those of the general formula (I) in which

A represents oxiranyl, which is optionally substituted by straight-chain or branched alkyl having up to 7 carbon atoms, which in turn can be substituted by phenyl, or represents a radical of the formula

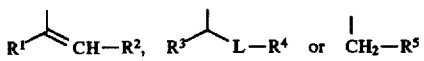

wherein $R^1$ denotes hydrogen or straight-chain or branched alkyl having up to 5 carbon atoms, $R^2$ denotes straight-chain or branched alkyl having up to 6 carbon atoms, which is optionally substituted by phenyl, $R^3$ denotes straight-chain or branched alkyl having up to 4 carbon atoms or a group of the formula —$OR^6$,
wherein $R^6$ denotes hydrogen, benzyl, acetyl or straight-chain or branched alkyl having up to 4 carbon atoms, $R^4$ denotes straight-chain or branched alkyl having 2 to 8 carbon atoms, which is optionally substituted by phenyl, L denotes a radical of the formula —CO—, —CH(OH), —CH$_2$, —CH(N$_3$) or —CH(OSO$_2$R$^7$), wherein R$^7$ denotes straight-chain or branched alkyl having up to 3 carbon atoms or phenyl, R$^5$ denotes straight-chain or branched alkyl having 3 to 7 carbon atoms, which is optionally substituted by phenyl, or denotes benzyl or 2-phenylethyl, D represents hydrogen, or represents a group of the formula —SO$_2$—NR$^8$R$^9$, wherein R$^8$ and R$^9$ are identical or different and denote hydrogen, phenyl or straight-chain or branched alkyl having up to 5 carbon atoms, which is optionally substituted by hydroxyl, or, together with the nitrogen atom, form a morpholinyl, piperidinyl or piperazinyl ring, which is optionally substituted, including via a free N function, by straight-chain or branched alkyl having up to 4 carbon atoms, which in turn can be substituted by hydroxyl, and E represents straight-chain or branched alkyl having up to 6 carbon atoms, and tautomers and salts thereof.

Particularly preferred compounds are those of the general formula (I) in which

A represents oxiranyl, which is optionally substituted by straight-chain or branched alkyl having up to 6 carbon atoms, which in turn can be substituted by phenyl, or represents a radical of the formula

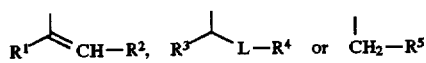

wherein

R$^1$ denotes hydrogen or straight-chain or branched alkyl having up to 3 carbon atoms, R$^2$ denotes straight-chain or branched alkyl having up to 6 carbon atoms, which is optionally substituted by phenyl, R$^3$ denotes straight-chain or branched alkyl having up to 4 carbon atoms or a group of the formula —OR$^6$, wherein R$^6$ denotes hydrogen, benzyl, acetyl or straight-chain or branched alkyl having up to 3 carbon atoms, R$^4$ denotes straight-chain or branched alkyl having 2 to 7 carbon atoms, which is optionally substituted by phenyl, L denotes a radical of the formula —CO—, —CH(OH), —CH$_2$, —CH(N$_3$) or —CH(OSO$_2$R$^7$), wherein R$^7$ denotes straight-chain or branched alkyl having up to 3 carbon atoms or phenyl, R$^5$ denotes straight-chain or branched alkyl having 3 to 6 carbon atoms, which is optionally substituted by phenyl, or denotes benzyl or 2-phenylethyl, D represents hydrogen, or represents a group of the formula —SO$_2$—NR$^8$R$^9$, wherein R$^8$ and R$^9$ are identical or different and denote hydrogen, phenyl or straight-chain or branched alkyl having up to 3 carbon atoms, or, together with the nitrogen atom, form a morpholinyl or piperidinyl ring, and E represents straight-chain or branched alkyl having up to 4 carbon atoms, and tautomers and salts thereof.

A process has furthermore been found for the preparation of the compounds of the general formula (I) according to the invention, characterized in that compounds of the general formula (II)

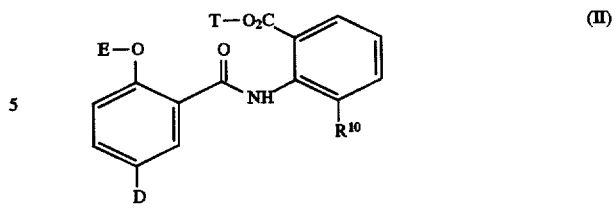

in which

D and E have the abovementioned meaning,

T represents C$_1$-C$_4$-alkyl and

R$^{10}$ represents halogen, preferably bromine or iodine, are first cyclized with formamide to give the compounds of the general formula (III)

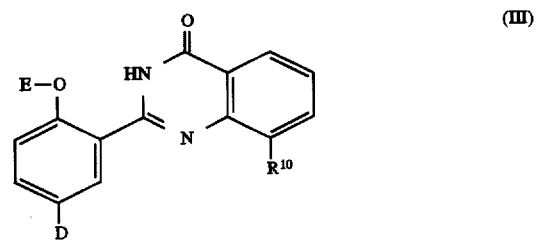

in which

D, E and R$^{10}$ have the abovementioned meaning; and in a last step, these are converted with compounds of the general formula (IV)

in which

R$^1$ and R$^2$ have the abovementioned meaning, in inert solvents in the presence of a base and in the system of tri-o-tolylphosphine/palladium(II) acetate, into the compounds of the general formula (Ia)

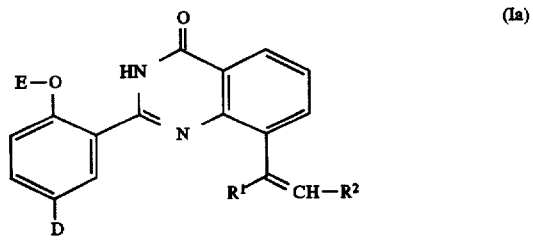

in which

D,E,R$^1$ and R$^2$ have the abovementioned meaning, and if appropriate the double bond is hydrogenated, or, in the case where A=substituted oxiranyl, if appropriate the double bond is oxidized by customary methods with an oxidizing agent in inert solvents to give the corresponding epoxide compounds, and these are converted into the corresponding hydroxy compounds by ring-opening reactions, and, starting from the hydroxy compounds, if appropriate after activation, nucleophilic substitution reactions are carried out, or the hydroxy compounds are oxidized to the oxo compounds.

The process according to the invention can be illustrated by way of example by the following equation:

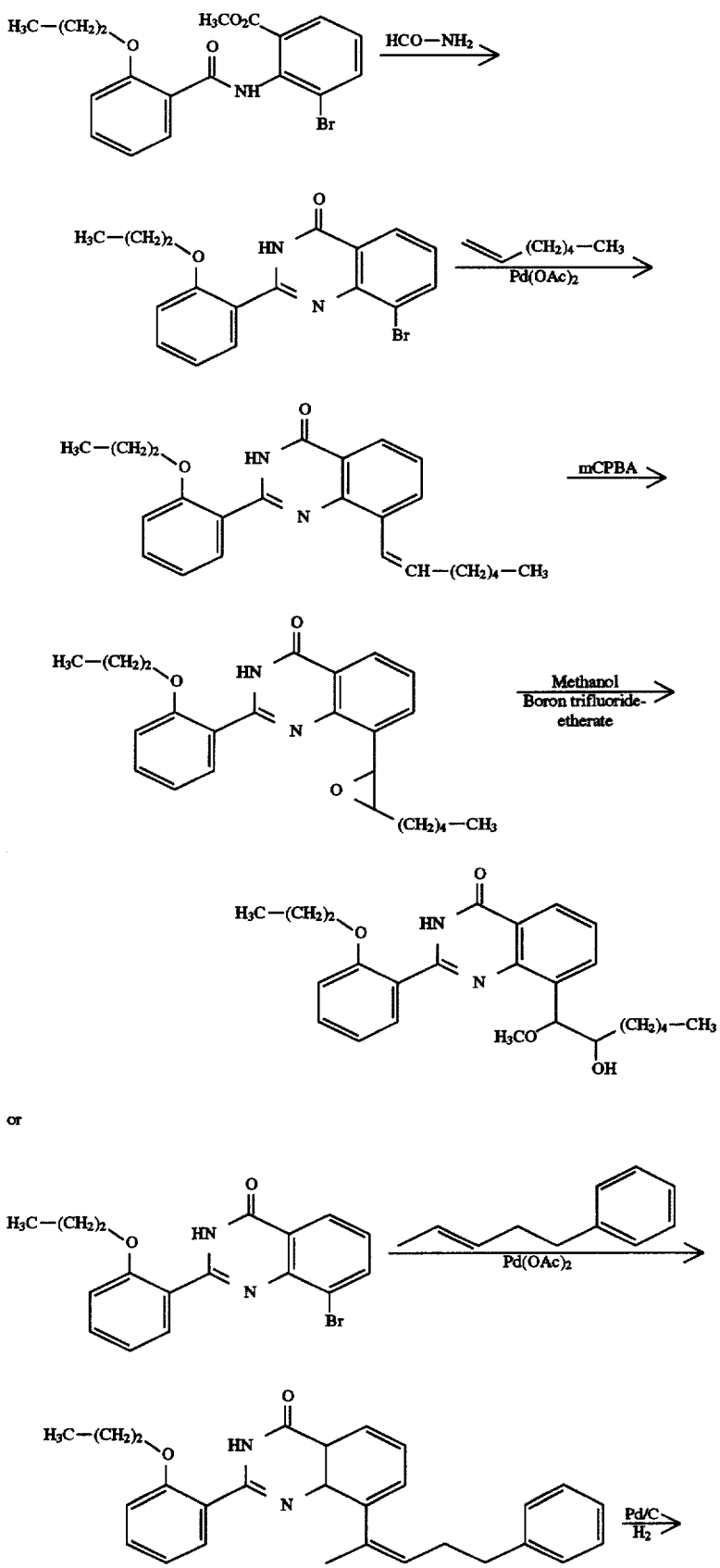

-continued

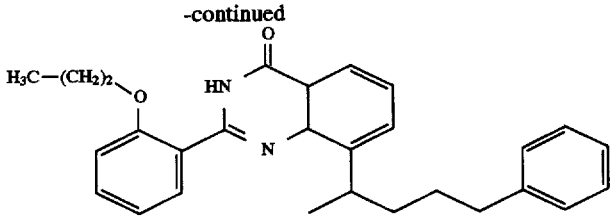

Inert organic solvents which do not change under the reaction conditions are suitable for the process. These include, preferably, ethers, such as, for example, diethyl ether, dioxane, tetrahydrofuran or glycol mono- or dimethyl ether, halogenated hydrocarbons, such as methylene chloride, chloroform or carbon tetrachloride, dichloroethylene or trichloroethylene, ethyl acetate, toluene, acetonitrile, dimethylformamide, hexamethylphosphoric acid triamide and acetone. It is of course possible to employ mixtures of the solvents. Methylene chloride and dimethylformamide are particularly preferred.

The reaction temperature can in general be varied within a relatively wide range. The reaction is in general carried out in a range from –20° C. to 200° C., preferably 0° C. to 25° C.

The cyclization is in general carried out in a temperature range from +50° C. to 200° C., preferably +160° C. to +180° C.

The preparation of the compounds of the general formula (Ia) is in general carried out in one of the abovementioned solvents, preferably dimethylformamide, and in the presence of a base.

Bases which can be employed are in general inorganic or organic bases. These include, preferably, alkali metal carbonates, such as sodium carbonate, potassium carbonate or caesium carbonate, or alkali metal or alkaline earth metal alcoholates or amides, such as sodium or potassium methanolate, sodium or potassium ethanolate, potassium tert-butylate or potassium amide, or organic amines (trialkyl ($C_1$–$C_6$)amines), such as triethylamine or tributylamine. Tributylamine is particularly preferred.

The bases are in general employed in an mount of 0.05 mol to 10 mol, preferably 1 mol to 2 mol, per mole of the compound of the formula (III).

The process according to the invention is in general carried out in a temperature range from 0° C. to +180° C., preferably +30° C. to +150° C.

The process steps according to the invention are in general carried out under normal pressure. However, it is also possible to carry out the process steps under increased pressure or under reduced pressure (for example in a range from 0.5 to 5 bar).

The epoxidation is carried out in one of the abovementioned solvents, preferably dry chloroform, in the presence of an oxidizing agent, such as, for example, m-chloroperbenzoic acid or $H_2O_2$. m-Chloroperbenzoic acid is preferred.

The epoxidation is in general carried out in a temperature range from –20° C. to +50° C., preferably 0° C. to +30° C.

The hydrogenation is in general carried out in one of the abovementioned alcohols, preferably methanol.

Palladium compounds are in general suitable as the catalyst. Pd/C is preferred.

The catalyst is employed in an amount of 0.01 mol to 0.4 mol, preferably 0.05 mol to 0.2 mol, per mole of the corresponding alcohol.

The hydrogenation is in general carried out in a temperature range from –20° C. to +50° C., preferably 0° C. to +30° C.

The hydrogenation is in general carried out under normal pressure. However, it is also possible to carry out the hydrogenation under increased pressure or under reduced pressure (for example in a range from 0.5 to 5 bar).

The epoxide openings are carried out by the method described in the literature [cf. Takano et al., Heterocycles 29, (1989), 249] and likewise in one of the abovementioned alcohols, preferably methanol, in the presence of boron trifluoride-etherate.

The reaction with alkylsulphonic acid chlorides is carried out, starting from the corresponding free hydroxy compounds, in one of the abovementioned solvents and one of the bases, preferably with methylene chloride and triethylamine, in a temperature range from –20° C. to +20° C., preferably 0° C., under normal pressure.

The introduction of the azide radical is in general carried out by reaction of the corresponding alkylsulphonyloxy-substituted compounds with sodium azide in one of the abovementioned solvents, preferably dimethylformamide, in a temperature range from 50° C. to +120° C., preferably 100° C., under normal pressure.

The ketones are prepared by known methods (Swern oxidation), starting from the corresponding hydroxy compounds.

The enantiomerically pure compounds are accessible by customary methods, for example by chromatography of the racemic compounds of the general formula (I) on chiral phases.

The compounds of the general formula (II) are known in some cases or are new, and can then be prepared by a procedure in which compounds of the general formula (V)

(V)

in which $R^{10}$ and T have the abovementioned meaning, are reacted with 2-n-alkoxylbenzoic acid chlorides of the formula (VI)

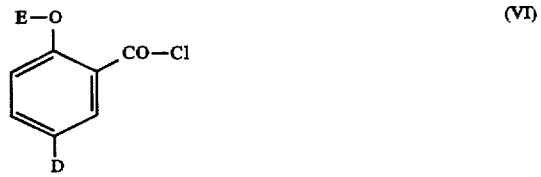

(VI)

in which

D and E have the abovementioned meaning, in inert solvents and in the presence of a base.

Suitable solvents are the abovementioned solvents, methylene chloride being preferred.

Suitable bases are cyclic amines, such as, for example, piperidine, pyridine, pyrimidine or dimethylaminopyridine, or $C_1$–$C_4$-alkylamines, such as, for example, triethylamine. Triethylamine and pyridine are preferred.

The base is in general employed in an amount of 0.5 mol to 2 mol, preferably 1 mol to 1.2 mol, in each case per mole of the compounds of the general formula (V).

The reaction temperature can in general be varied within a relatively wide range. The reaction is in general carried out in a range from −20° C. to 200° C., preferably 0° C. to 25° C.

The compounds of the general formulae (V) (for example J. Heterocyclic. Chem., 26(5), 1989, 1405–1413) and (VI) (for example EP-0 526 004 A1) are known per se.

The compounds of the general formula (III) are new and can be prepared as described above.

The compounds of the general formula (IV) are known.

The compounds of the general formula (Ia) are new and can be prepared as described above.

The compounds of the general formula (I) and (Ia) according to the invention display an unforeseeable valuable pharmacological action spectrum.

They inhibit either one or more of the cGMP-metabolizing phosphodiesterases (PDE I, PDE II and PDE V). This leads to a differentiated rise in cGMP. An increase in the cGMP level can lead to an antithrombotic, vasodilatory, antiarrhythmic and/or antiinflammatory action. The selectivity is also determined by the distribution of the isoenzymes in the tissue.

The compounds according to the invention furthermore intensify the action of substances, such as, for example, EDRF (endothelium-derived relaxing factor) and ANP (atrial natriuretic peptide), which increase the cGMP level.

They can therefore be employed in medicaments for treatment of inflammatory diseases, such as, for example, asthma, inflammatory dermatoses, for treatment of high blood pressure, stable and unstable angina, peripheral and cardial vascular diseases and of arrhythmias, for treatment of thromboembolic diseases and ischaemias, such as myocardial infarction, cerebral stroke, transitory and ischaemic attacks, angina pectoris, peripheral circulatory disturbances, prevention of restenoses, such as after thrombolysis treatments, percutaneous transluminal angioplasties (PTA) and bypass, percutaneous transluminal coronary angioplasties (PTCA), bypass, septic shock and diseases of the urogenital system, such as, for example, prostate hypertrophy, impotence and incontinence.

Activity of the phosphodiesterases (PDEs)

The cGMP-stimulatable PDE II, the cGMP-inhibitable PDE III and the cAMP-specific PDE IV were isolated from either porcine or bovine myocardia. The Ca-calmodulin-stimulatable PDE I was isolated from the porcine aorta or porcine brain. The cGMP-specific PDE V was obtained from the porcine intestine, porcine aorta and/or human blood platelets. Purification was carried out by anion exchange chromatography on MonoQ$^R$ Pharmacia, essentially by the method of M. Hoey and Miles D. Houslay, Biochemical Pharmacology, Volume 40, 193–202 (1990).

The enzyme activity is determined in a test batch of 100 μl in 20 mM Tris/HCl buffer of pH 7.5 which contains 5 mM MgCl$_2$, 0.1 mg/ml of bovine serum albumin and either 800 Bq of $^3$HcAMP or $^3$HcGMP. The final concentration of the corresponding nucleotide is $10^{-6}$ mol/l. The reaction is started by addition of the enzyme and the amount of enzyme is chosen such that about 50% of the substrate is converted during the incubation time of 30 minutes. To test the cGMP-stimulatable PDE II, $^3$HcAMP is used as the substrate and $10^{-6}$ mol/l of non-labelled cGMP is added to the batch. To test the Ca-calmodulin-dependent PDE I, 1 μM CaCl$_2$ and 0.1 μM calmodulin are also added to the reaction batch. The reaction is stopped by addition of 100 μl of acetonitrile which contains 1 mM cAMP and 1 mM AMP. 100 μl of the reaction batch are separated on the HPLC and the cleavage products are determined quantitatively "online" using a flow-through scintillation counter. The substance concentration at which the rate of reaction is reduced by 50% is measured.

| Inhibition of the phosphodiesterases in vitro | | | |
|---|---|---|---|
| Example No. | PDE I IC$_{50}$ [mM] | PDE II IC$_{50}$ [mM] | PDE V IC$_{50}$ [mM] |
| 14 | 5 | 5 | 3 |
| 15 | 3 | 5 | |
| 16 | | 5 | 5 |
| 20 | 10 | 2 | 5 |
| 29 | | 0.5 | 1 |

The compounds were investigated for antihypertensive activity on anaesthetized pigs.

The antihypertensive activity was measured after intravenous administration to SHR rats.

For determination of the cyclic nucleotides, heart and aorta tissue were removed and deep-frozen immediately. The examples were powdered under liquid N$_2$ and extracted with 70% ethanol and the content of cGMP and cAMP was determined by commercial radioimmunoassay (Amersham).

The erection-inducing action was measured on anaesthetized rabbits (C. G. Stief et al., World Journal Urology 1990, pages 233–236).

The substances were administered in dosages of 0.1 to 10 mg/kg either directly into the corpus cavernosum or intraduodenally, rectally, orally, transdermally or intravenously.

The new active compounds can be converted in a known manner into the customary formulations, such as tablets, coated tablets, pills, granules, aerosols, syrups, emulsions, suspensions and solutions, using inert, non-toxic, pharmaceutically suitable carriers or solvents. The therapeutically active compounds should in each case be present here in a concentration of about 0.5 to 90% by weight of the total mixture, i.e. in amounts which are sufficient to achieve the stated dosage range.

The formulations are prepared, for example, by extending the active compounds with solvents and/or carriers, if appropriate using emulsifying agents and/or dispersing agents, and, for example, in the case where water is used as the diluent, organic solvents can be used as auxiliary solvents if appropriate.

The formulations are administered in the customary manner, preferably orally, parenterally, transdermally, perlingually or intravenously.

In general, it has proved advantageous in the case of intravenous administration to administer amounts of about 0.01 to 10 mg/kg, preferably about 0.1 to 10 mg/kg, of body weight to achieve effective results.

Nevertheless, it may be necessary if appropriate to deviate from the amounts mentioned, and in particular as a function of the body weight or the nature of the administration mute, of the behaviour of the individual towards the medicament, of the nature of the formulation thereof and of the time or interval at which administration takes place. Thus, in some cases it may be sufficient to manage with less than the abovementioned minimum amount, while in other cases the upper limit mentioned must be exceeded. If relatively large amounts are administered, it may be advisable to divide these into several individual doses over the course of the day.

Starting Compounds

EXAMPLE I

Methyl 2-(2-n-Propoxybenzamido)-3-iodo-benzoate

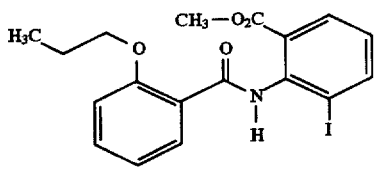

27.9 g (0.1 Mol) of methyl 2-amino-3-iodo-benzoate and 15.4 ml (0.11 mol) of triethylamine were dissolved in 170 ml of absolute $CH_2Cl_2$. A solution of 20 g (0.1 mol) of 2-n-propoxybenzoyl chloride in 80 ml of absolute $CH_2Cl_2$ was added dropwise at 0° C. The mixture was stirred overnight at 20° C., the precipitate was filtered off and the product was extracted by shaking with 100 ml of 1N HCl, 100 ml of 1N NaOH and 100 ml of saturated NaCl solution. The organic phase was dried over $Na_2SO_4$ and evaporated in vacuo and the residue was purified by chromatography over silica gel (eluent: toluene/ethyl acetate 95:5).
Yield: 36 g (81.4%)
$R_f$=0.25 (toluene/ethyl acetate 10:1)

EXAMPLE II

Methyl 2-(2-n-propoxybenzamido)-3-bromo-benzoate

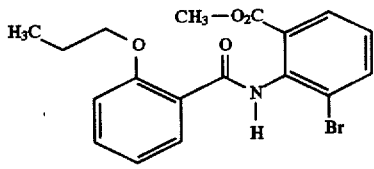

The title compound was prepared analogously to the instructions for Example I starting from methyl 2-amino-3-bromo-benzoate.
Yield: 60.4%
$R_f$=0.19 (toluene/ethyl acetate 5:1)

EXAMPLE III 2-(2-n-Propoxyphenyl)-8-iodo-quinazolin-4-(3H)-one

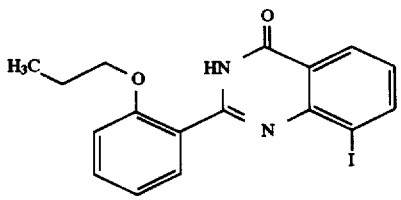

19.4 g (44.17 mmol) of the compound from Example I were stirred in 216 ml of formamide at 180° C. for 10 hours. After cooling, 500 ml of water were added and the mixture was extracted 4 times with 300 ml of $CH_2Cl_2$ each time. The combined organic phases were dried over $MgSO_4$, the solvent was evaporated in vacuo and the residue was stirred in a mixture of 100 ml of diethyl ether and 50 ml of petroleum ether. The product was filtered off with suction (17.8 g) and recrystallized from 250 ml of absolute ethanol.
Yield: 14.56 g (81.2%)
Melting point: 174° C.

EXAMPLE IV 2-(2-n-Propoxyphenyl)-8-bromo-quinazolin-4-(3H)-one

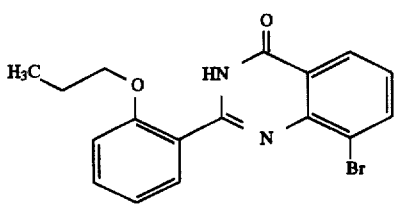

The title compound was prepared analogously to the instructions for Example III starting from the compound from Example II.
Yield: 60%
$R_f$=0.7 (toluene/ethyl acetate 10:1)

Preparation Examples

EXAMPLE 1

2-(2-n-Propoxyphenyl)-8-(1-hepten-1-yl)-quinazolin-4 (3H)-one

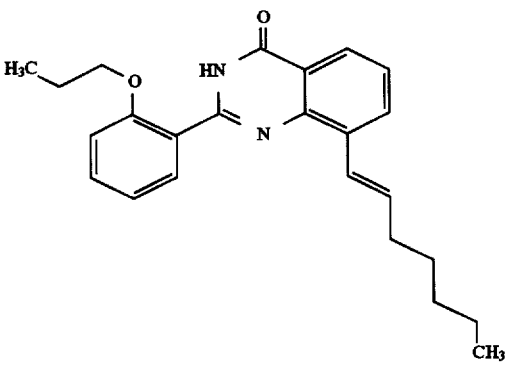

5 g (12.31 mmol) of the compound from Example III, 3.7 ml (15.4 mmol) of tributylamine, 6.6 ml (46.2 mmol) of 1-heptene, 375 mg of tri-o-tolylphosphine (1.23 mmol) and 138 mg of palladium(II) acetate (0.6 mmol) were stirred in 50 ml of dry dimethylformamide at 100° C. for 2.5 hours. The mixture was cooled to room temperature and, after addition of 50 ml of ethyl acetate, was washed 3 times with 50 ml of $H_2O$ each time. After drying over $MgSO_4$, the organic phase was evaporated in vacuo and the residue was chromatographed over silica gel using toluene/ethyl acetate 95:5 as the eluent. The fractions containing the product were combined and the solvent was evaporated in vacuo. The initially oily residue was crystallized by stirring with 35 ml of petroleum ether.
Yield: 2.2 g (47.5%)
Melting point: 94° C.

EXAMPLE 2

2-(2-n-Propoxyphenyl)-8-(3-phenyl-1-propen-1-yl)-quinazolin-4(3H)-one

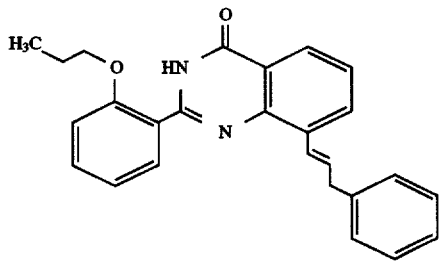

The title compound was obtained analogously to the instructions of Example 1 starting from the compound of Example III and 3-phenyl-1-propene.
Yield: 63.9%
Melting point: 123°–126° C. (from diethyl ether)

EXAMPLE 3

2-(2-n-Propoxyphenyl)-8-(4-phenyl-1-buten-1-yl)-quinazolin-4(3H)-one

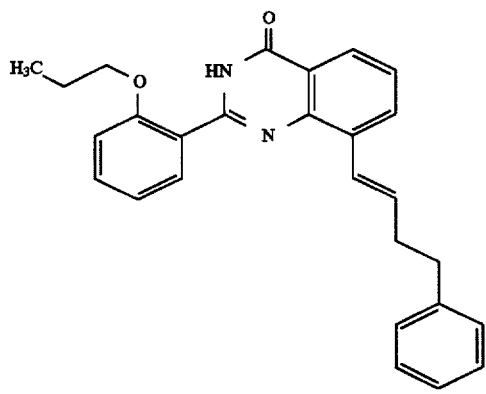

The title compound was obtained analogously to the instructions for Example 2 starting from the compound from Example III and 4-phenyl-1-butene.
Yield: 49.9%.
$R_f$=0.27 (toluene/ethyl acetate 10:1)

EXAMPLE 4 and EXAMPLE 5

2-(2-n-Propoxyphenyl)-8-(5-phenyl-2-penten-2-yl)-quinazolin-4(3H)-one and 2-(2-n-Propoxyphenyl)-8-(5-phenyl-3-penten-3-yl)-quinazolin-4(3H)-one

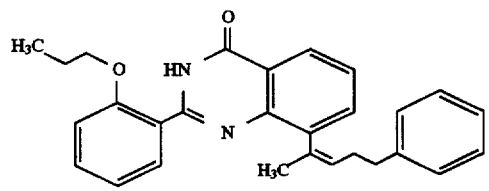

(4)

and

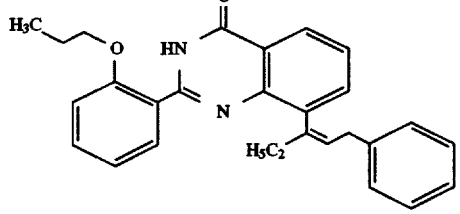

(5)

The title compounds were obtained analogously to the instructions of Example 1 starting from the compound from example III and 5-phenyl-2-pentene.
Yield: 64.6%
Mixture of the two isomers, which were hydrogenated without separation (cf. Example 8).

EXAMPLE 6

2-(2-n-Propoxyphenyl)-8-(1-heptyl)-quinazolin-4(3H)-one

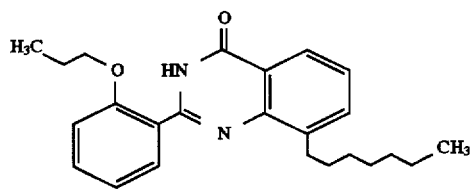

20 mg of Pd/C (10% strength) were prehydrogenated in 2 ml of absolute methanol for 20 minutes. 200 mg (0.53 mmol) of the compound from Example 1 in a mixture of 2 ml of absolute methanol and 0.8 ml of ethyl acetate were added and hydrogenation was carried out at 20° C. for 1 hour. The catalyst was filtered off and the solvent was removed on a rotary evaporator in vacuo. The residue was clean in the thin layer chromatogram and crystallized when dried under a high vacuum.
Yield: 180 mg (89.6%)
Melting point: 73° C.

EXAMPLE 7

2-(2-n-Propoxyphenyl)-8-(3-phenyl-1-propyl)-quinazolin-4(3H)-one

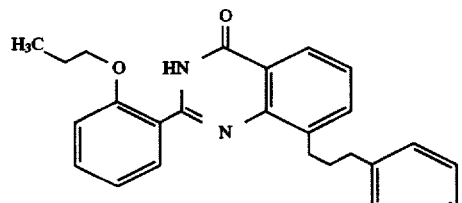

The title compound was prepared analogously to the instructions of Example 6 starting from the compound from Example 2.
Yield: 79.7%
Melting point: 89° C.

EXAMPLE 8

2-(2-n-Propoxyphenyl)-8-(4-phenyl-1-butyl)-quinazolin-4(3H)-one

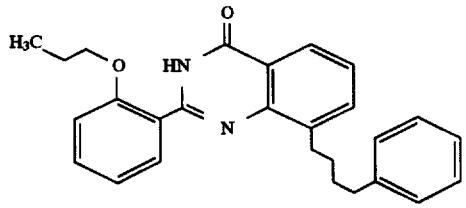

The title compound was prepared analogously to the instructions for Example 6 starting from the compound from Example 3.

Yield: 86.2%
Melting point: 82° C.

EXAMPLE 9 and EXAMPLE 10

2-(2-n-Propoxyphenyl)-8-(5-phenyl-2-pentyl)-quinazolin-4(3H)-one and 2-(2-n-Propoxyphenyl)-8-(5-phenyl-3-pentyl)-quinazolin-4(3H)-one

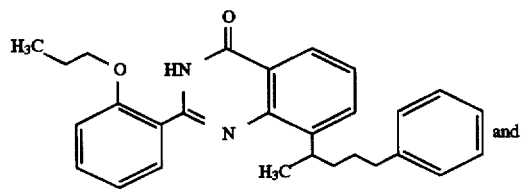

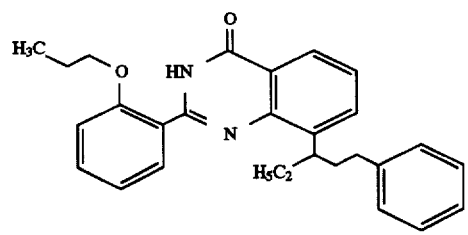

The title compounds were prepared analogously to the instructions of Example 6 starting from the isomer mixture from Example 4. The separation was carried out by medium pressure chromatography over silica gel using $CH_2Cl_2$/ethyl acetate (20:5) as the eluent.

Yield of Example 9: 9%
Yield of Example 10: 7.8%
$R_f$ of Example 9: 0.49 ($CH_2Cl_2$/ethyl acetate 10:1)
$R_f$ of Example 10: 0.51 ($CH_2Cl_2$/ethyl acetate 10:1)

EXAMPLE 11

2-(2-n-Propoxyphenyl)-8-(1,2-epoxy-1-heptyl)-quinazolin-4(3H)-one

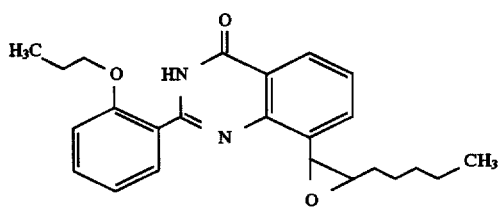

1.5 g (3.98 mmol) of the compound from Example 1 were dissolved in 40 ml of dry chloroform at 0° C. 0.98 g (3.98 mmol) of 70% strength m-chloroperbenzoic acid was added. The mixture was allowed to come to room temperature and was subsequently stirred for 3 hours. It was washed 3 times with 30 ml of 10% strength sodium bisulphite solution each time and twice with 30 ml of 1N NaOH solution each time, dried over $MgSO_4$ and evaporated in vacuo. The residue (1.6 g) was chromatographed over silica gel using toluene/ethyl acetate 95:5 as the eluent.
Yield: 1.06 g (67.8%)
Melting point: 78° C.

EXAMPLE 12

2-(2-n-Propoxyphenyl)-8-(3-phenyl-1,2-epoxy-1-propyl)-quinazolin-4(3H)-one

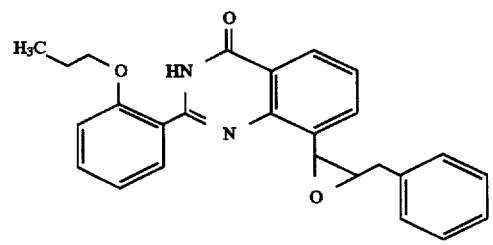

The title compound was prepared analogously to the instructions for Example 11 starting from the compound from Example 2.
Yield: 47%
$R_f$=0.27 (toluene/ethyl acetate 10:1)

EXAMPLE 13

2-(2-n-Propoxyphenyl)-8-(4-phenyl-1,2-epoxy-1-butyl)-quinazolin-4(3H)-one

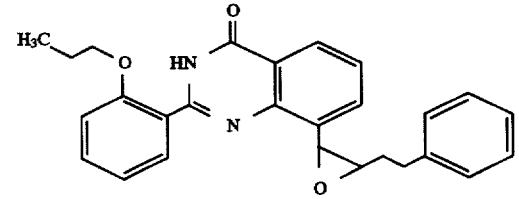

The title compound was prepared analogously to the instructions for Example 11 starting from the compound from Example 3.
Yield: 61.4%
$R_f$=0.29 (toluene/ethyl acetate 1:1)

EXAMPLE 14

2-(2-n-Propoxyphenyl)-8-(1-methoxy-2-hydroxy-1-heptyl)-quinazolin-4(3H)-one

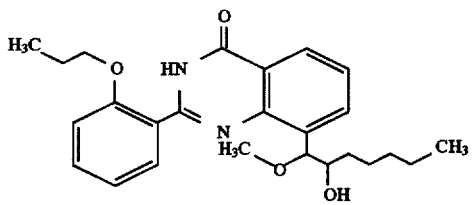

0.1 ml of boron trifluoride-etherate (0.76 mmol) was added dropwise to a solution of 0.2 g (0.51 mmol) of the compound from Example 11 in 6 ml of methanol at 0° C. After 20 minutes at 0° C., 75 ml of ethyl acetate were added and the mixture was extracted by shaking 3 times with 50 ml of water each time. The organic phase was chromatographed over silica gel using toluene/ethyl acetate 5:1 as the eluent.
Yield: 160 mg (73.9%)
$R_f$=0.19 (toluene/ethyl acetate 5:1)

EXAMPLE 15

2-(2-n-Propoxyphenyl)-8-(3-phenyl-1-methoxy-2-hydroxy-1-propyl)-quinazolin-4(3H)-one

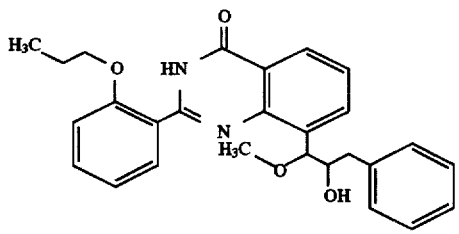

The title compound was prepared analogously to the instructions for Example 14 starting from the compound from Example 12.
Yield: 32.5%
$R_f$=0.20 (toluene/ethyl acetate 5:1)

EXAMPLE 16

2-(2-n-Propoxyphenyl)-8-(4-phenyl-1-methoxy-2-hydroxy-1-butyl)-quinazolin-4(3H)-one

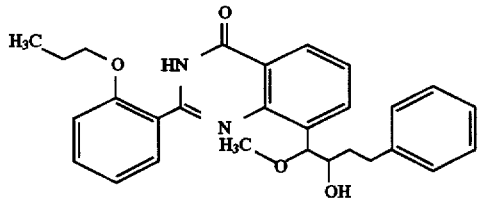

The title compound was prepared analogously to the instructions for Example 14 starting from the compound from Example 10.
Yield: 74.4%
$R_f$=0.17 (toluene/ethyl acetate 5:1)

EXAMPLE 17

2-(2-n-Propoxyphenyl)-8-(3-hydroxy-2-octyl)-quinazolin-4(3H)-one

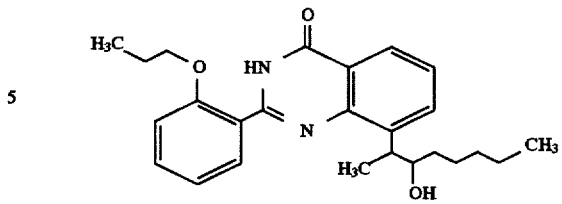

1.9 ml of 1.6 molar methyllithium solution in diethyl ether (3.06 mmol) were added dropwise to a suspension of 0.14 g (1.53 mmol) of Cu(I)CN in 3 ml of absolute diethyl ether at −78° C. After 1 hour at −78° C., the mixture was warmed to −45° C. and 200 mg (0.51 mmol) of the compound from Example 11 in 2 ml of absolute diethyl ether were added dropwise. The mixture was stirred at 0° C. for 1 hour and then at 20° C. until the reaction had ended (monitoring by thin layer chromatography, about 1 hour). After addition of 50 ml of ethyl acetate, the mixture was washed 3 times with 30 ml of water each time. The organic phase was dried over $Na_2SO_4$ and evaporated on a rotary evaporator in vacuo. The residue was chromatographed over silica gel using toluene/ethyl acetate 7:1 as eluent.
Yield: 80 mg (38.4%)
$R_f$=0.22 (toluene/ethyl acetate 5:1)

EXAMPLE 18

2-(2-n-Propoxyphenyl)-8-(4-phenyl-3-hydroxy-2-butyl)-quinazolin-4(3H)-one

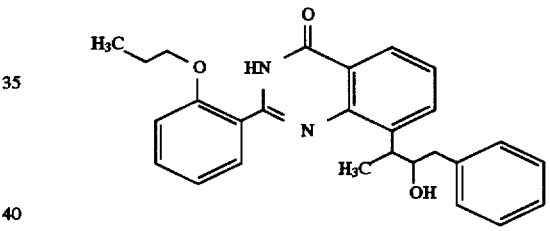

The title compound was prepared analogously to the instructions for Example 14 starting from the compound from Example 9.
Yield: 38.5%
$R_f$=0.21 (toluene/ethyl acetate 5:1)

EXAMPLE 19

2-(2-n-Propoxyphenyl)-8-(5-phenyl-3-hydroxy-2-pentyl)-quinazolin-4(3H)-one

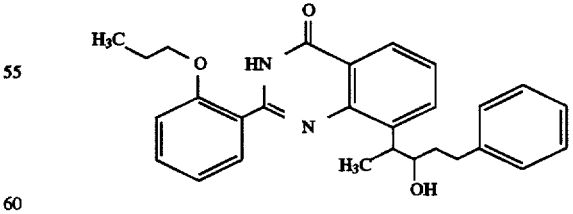

The title compound was prepared analogously to the instructions for Example 17 starting from the compound from Example 13.
Yield: 51.4%
Diasteromer mixture, $R_f$=0.18 and 0.24 (toluene/ethyl acetate 5:1)

EXAMPLE 20

2-(2-n-Propoxyphenyl)-8-(4-hydroxy-3-nonyl)-quinazolin-4(3H)-one

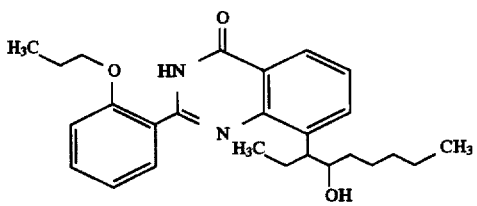

1.02 ml of a 3M C₂H₅MgBr solution (3.05 mmol) in diethyl ether was added dropwise to a solution of 240 mg (0.61 mmol) of the compound from Example 11 at −20° C. and the mixture was stirred at −20° C. for 45 minutes and then at room temperature for 20 minutes. The oily precipitate was dissolved by addition of 4 ml of absolute tetrahydrofuran and 1.02 ml of the 3M C₂H₅MgBr solution were added once more to bring the reaction to completion. After 15 minutes at 20° C., 75 ml of ethyl acetate were added and the mixture was extracted by shaking 3 times with 50 ml of water each time. After the organic phase had been dried over MgSO₄, the solvent was removed on a rotary evaporator in vacuo and the residue was chromatographed over silica gel using toluene/ethyl acetate 10:1 as the eluent.

Yield: 40 mg (15.5%)
$R_f$=0.24 (toluene/ethyl acetate 5:1)

EXAMPLE 21

2-(2-n-Propoxyphenyl)-8-(3-methanesulfonyloxy-2-octyl)-quinazolin-4(3H)-one

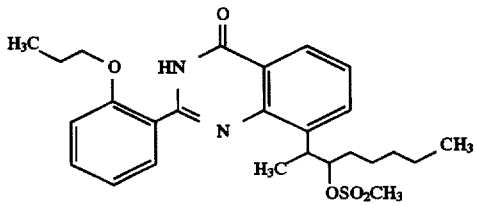

0.17 ml (2.17 mmol) of methanesulphonyl chloride was added to 740 mg (1.81 mmol) of the compound from Example 17 and 0.3 ml (2.17 mmol) of triethylamine in 18 ml of absolute CH₂Cl₂ at 0° C. The mixture was allowed to come to room temperature and was subsequently stirred for 30 minutes. It was extracted by shaking twice with 30 ml of 1N NaOH each time and twice with 30 ml of 1N HCl each time, the organic phase was dried over MgSO₄ and the solvent was removed on a rotary evaporator in vacuo. The solid residue was stirred in a mixture of 30 ml of ethyl acetate and 30 ml of petroleum ether and the product was filtered off.

Yield: 650 mg (73.8%)
Melting point: 195° C.

EXAMPLE 22

2-(2-n-Propoxyphenyl)-8-(3-azido-2-octyl)-quinazolin-4(3H)-one

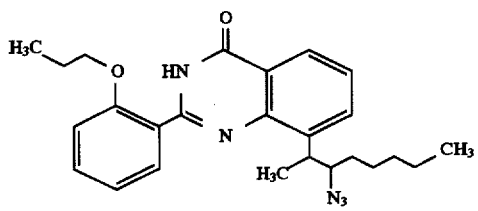

50 mg (0.103 mmol) of the compound from Example 18 and 13.4 ml (0.206 mmol) of sodium azide were stirred in 2 ml of absolute dimethylformamide at 40° C. overnight. 5 ml of ethyl acetate were added and the mixture was extracted by shaking 3 times with 50 ml of water each time. After the organic phase had been dried over Na₂SO₄, the solvent was removed on a rotary evaporator in vacuo and the residue was purified by flash chromatography over silica gel (eluent: tolene/ethyl acetate 5:1).

Yield: 31 mg (67%)
$R_f$=0.59 (toluene/ethyl acetate 5:1)

Example 23

2-(2-n-Propoxyphenyl)-8-(1-methoxy-2-oxo-1-heptyl)-quinazolin-4(3H)-one

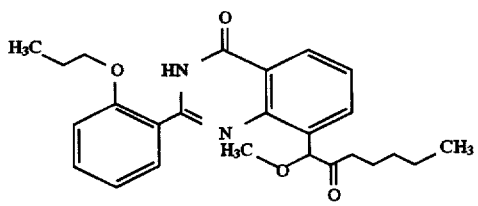

0.38 ml (5.41 mmol) of absolute dimethyl sulphoxide in 4 ml of absolute CH₂Cl₂ was added dropwise to 0.21 ml (2.46 mmol) of oxalyl chloride in 13 ml of absolute CH₂Cl₂ at −70° C. After 30 minutes, 870 mg (2.05 mmol) of the compound from Example 14 in 6 ml of absolute CH₂Cl₂ were added dropwise, and after a further 30 minutes 1.42 ml (10.24 mmol) of N(C₂H₅)₃ were added dropwise. The mixture was allowed to come to room temperature, and after 10 minutes 100 ml of H₂O were added. The aqueous phase was extracted 3 times with 50 ml of CH₂Cl₂ each time and the combined CH₂Cl₂ phases were dried over MgSO₄ and concentrated on a rotary evaporator. The residue was dissolved in 10 ml of ethanol and, after addition of 3 ml of 1N HCl, the mixture was stirred at room temperature for 3 hours. The ethanol evaporated off in vacuo, the residue was taken up in 30 ml of ethyl acetate and the mixture was washed twice with H₂O. After drying over MgSO₄, the mixture was evaporated on a rotary evaporator in vacuo and the residue was purified by chromatography over silica gel using toluene/ethyl acetate 98:2 as the eluent.

Yield: 510 mg (58.9%)
$R_f$=0.26 (toluene/ethyl acetate 5:1).

EXAMPLE 24

2-(2-n-Propoxy-5-morpholinosulphonylphenyl)-8-(1-hepten-1-yl)-quinazolin-4(3H)-one

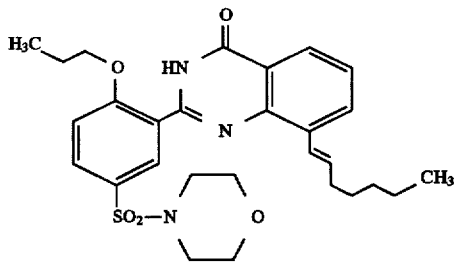

The title compound was prepared analogously to the instructions of Example 1 starting from 2-(2-n-propoxy-5-morpholinosulphonylphenyl)-8-bromoquinazolin-4-(3H)-one and 1-heptene.
Yield: 53.2%
Melting point: 112° C. (diethyl ether)

EXAMPLE 25

2-(2-n-Propoxy-5-morpholinosulphonylphenyl)-8-(1,2-epoxy-1-heptyl)-quinazolin-4-(3H)-one

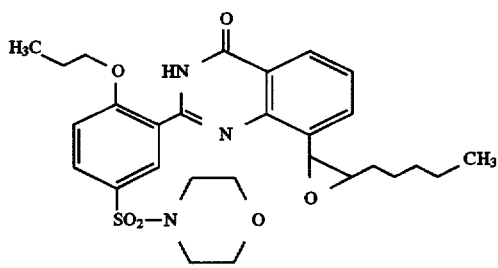

The title compound was prepared analogously to the instructions of Example 11 starting from the compound from Example 24.
Yield: 90.7%
Melting point: 96° C.

EXAMPLE 26

2-(2-n-Propozy-5-morpholinosulphonylphenyl)-8-(1-methoxy-2-hydroxy-1-heptyl)-quinazolin-4-(3H)-one

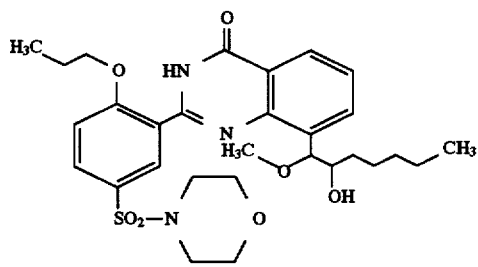

The title compound was prepared analogously to the instructions of Example 14 starting from the compound from Example 25.
Yield: 20.3%
$R_f$=0.42 (toluene/ethyl acetate 2:1)

EXAMPLE 27 and EXAMPLE 28

2-(2-n-Propoxy-5-morpholinosulphonylphenyl)-8-(5-phenyl-2-penten-2-yl)-quinazolin-4-(3H)-one and 2-(2-n-propoxy-5-morpholinosulphonylphenyl)-8-(5-phenyl-3-penten-3-yl)-quinazolin-4-(3H)-one

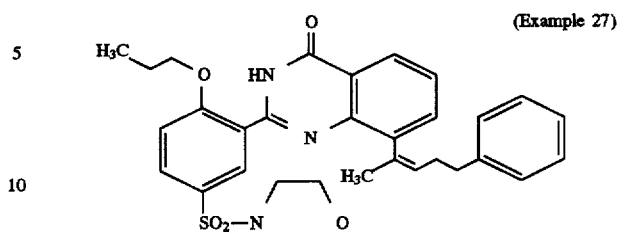
(Example 27)

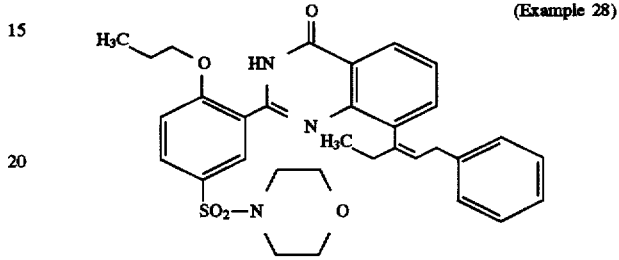
(Example 28)

The title compounds were obtained analogously to the instructions of Example 1 starting from 2-(2-n-propoxy-5-morpholinosulphonylphenyl)-8-bromoquinazolin-4-(3H)-one and 5-phenyl-2-pentene.
Yield: 39%
Mixture of the two isomers, which were hydrogenated without separation.

EXAMPLE 29 and EXAMPLE 30

2-(2-n-Propoxy-5-morpholinosulphonylphenyl)-8-(5-phenyl-2-pentyl)-quinazolin-4-(3H)-one and 2-(2-n-Propoxy-5-morpholiphosulphonylphenyl)-8-(5-phenyl-3-pentyl)-quinazolin-4-(3H)-one

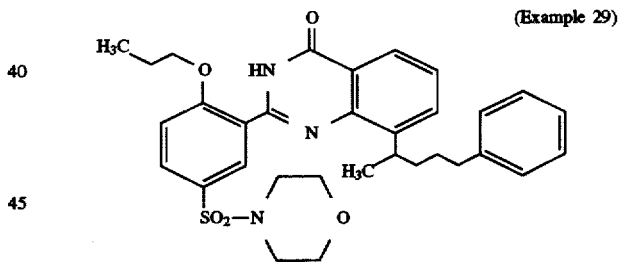
(Example 29)

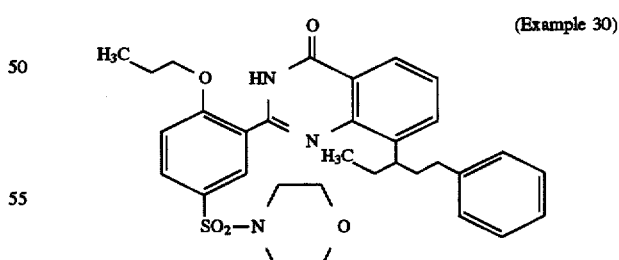
(Example 30)

The title compounds were prepared analogously to the instructions of Example 6 starting from the isomer mixtures from Example 27. Separation was carried out by medium pressure chromatography over silica gel using $CH_2Cl_2$/ethyl acetate (2:1) as the eluent.
Yield of Example 29: 36.3% $R_f$=0.44 ($CH_2Cl_2$/ethyl acetate 4:1)
Yield of Example 30: 18.4% $R_f$=0.49 ($CH_2Cl_2$/ethyl acetate 4:1)

We claim:
1. 2,8-Disubstituted quinazolinones of the general formula (I)

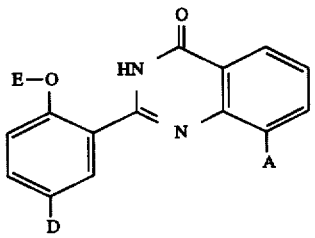

in which

A represents oxiranyl, which is optionally substituted by straight-chain or branched alkyl having up to 8 carbon atoms, which in turn can be substituted by phenyl, or represents a radical of the formula

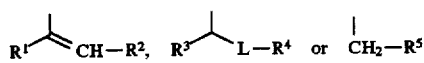

wherein $R^1$ denotes hydrogen or straight-chain or branched alkyl having up to 6 carbon atoms, $R^2$ denotes straight-chain or branched alkyl having up to 8 carbon atoms, which is optionally substituted by phenyl, $R^3$ denotes straight-chain or branched alkyl having up to 5 carbon atoms or a group of the formula —$OR^6$, wherein $R^6$ denotes hydrogen, a hydroxyl-protecting group or straight-chain or branched alkyl having up to 5 carbon atoms, $R^4$ denotes straight-chain or branched alkyl having 2 to 10 carbon atoms, which is optionally substituted by phenyl, L denotes a radical of the formula —CO—, —CH(OH), —$CH_2$, —$CH(N_3)$ or —$CH(OSO_2R^7)$, wherein $R^7$ denotes straight-chain or branched alkyl having up to 4 carbon atoms or phenyl, $R^5$ denotes straight-chain or branched alkyl having 3 to 8 carbon atoms which is substituted by phenyl, or denotes benzyl or 2-phenylethyl, D represents hydrogen, or represents a group of the formula —$SO_2$—$NR^8R^9$, wherein $R^8$ and $R^9$ are identical or different and denote hydrogen, phenyl or straight-chain or branched alkyl having up to 6 carbon atoms, which is optionally substituted by hydroxyl, or, together with the nitrogen atom, form a 5- to 6-membered saturated heterocyclic radical which has up to 2 further hetero atoms from the series consisting of S, N and/or O and is optionally substituted, including via a free N function, by straight-chain or branched alkyl having up to 6 carbon atoms, which in turn can be substituted by hydroxyl, and E represents straight-chain or branched alkyl having up to 8 carbon atoms, and tautomers and salts thereof.

2. 2,8-Disubstituted quinazolinones of the formula according to claim 1, in which A represents oxiranyl, which is optionally substituted by straight-chain or branched alkyl having up to 7 carbon atoms, which in turn can be substituted by phenyl, or represents a radical of the formula

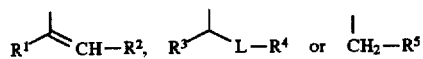

wherein $R^1$ denotes hydrogen or straight-chain or branched alkyl having up to 5 carbon atoms, $R^2$ denotes straight-chain or branched alkyl having up to 6 carbon atoms, which is optionally substituted by phenyl, $R^3$ denotes straight-chain or branched alkyl having up to 4 carbon atoms or a group of the formula —$OR^6$, wherein $R^6$ denotes hydrogen, benzyl, acetyl or straight-chain or branched alkyl having up to 4 carbon atoms, $R^4$ denotes straight-chain or branched alkyl having 2 to 8 carbon atoms, which is optionally substituted by phenyl, L denotes a radical of the formula —CO—, —CH(OH), —$CH_2$, —$CH(N_3)$ or —$CH(OSO_2R^7)$, wherein $R^7$ denotes straight-chain or branched alkyl having up to 3 carbon atoms or phenyl, $R^5$ denotes straight-chain or branched alkyl having 3 to 7 carbon atoms which is substituted by phenyl, or denotes benzyl or 2-phenylethyl, D represents hydrogen, or represents a group of the formula —$SO_2$—$NR^8R^9$, wherein $R^8$ and $R^9$ are identical or different and denote hydrogen, phenyl or straight-chain or branched alkyl having up 5 carbon atoms, which is optionally substituted by hydroxyl, or, together with the nitrogen atom, form a morpholinyl, piperidinyl or piperazinyl ring, which is optionally substituted, including via a free N function, by straight-chain or branched alkyl having up to 4 carbon atoms, which in turn can be substituted by hydroxyl, and E represents straight-chain or branched alkyl having up to 6 carbon atoms, and tautomers and salts thereof.

3. 2,8-Disubstituted quinazolinones of the formula according to claim 1, in which A represents oxiranyl, which is optionally substituted by straight-chain or branched alkyl having up to 6 carbon atoms, which in turn can be substituted by phenyl, or represents a radical of the formula

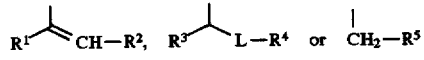

wherein $R^1$ denotes hydrogen or straight-chain or branched alkyl having up to 3 carbon atoms, $R^2$ denotes straight-chain or branched alkyl having up to 6 carbon atoms, which is optionally substituted by phenyl, $R^3$ denotes straight-chain or branched alkyl having up to 4 carbon atoms or a group of the formula —$OR^6$, wherein $R^6$ denotes hydrogen, benzyl, acetyl or straight-chain or branched alkyl having up to 3 carbon atoms, $R^4$ denotes straight-chain or branched alkyl having 2 to 7 carbon atoms which is optionally substituted by phenyl, L denotes a radical of the formula —CO—, —CH(OH)—, —CH$_2$, —CH(N$_3$) or —CH(OSO$_2$R$^7$), wherein R$^7$ denotes straight-chain or branched alkyl having up to 3 carbon atoms or phenyl, R$^5$ denotes straight-chain or branched alkyl having 3 to 6 carbon atoms which is substituted by phenyl, or denotes benzyl or 2-phenylethyl, D represents hydrogen, or represents a group of the formula —SO$_2$—NR$^8$R$^9$, wherein R$^8$ and R$^9$ are identical or different and denote hydrogen, phenyl or straight-chain or branched alkyl having up to 3 carbon atoms, or, together with the nitrogen atom, form a morpholinyl or piperidinyl ring, and E represents straight-chain or branched alkyl having up to 4 carbon atoms, and tautomers and salts thereof.

4. 2,8-disubstituted quinazolinoes according to claim 1 wherein such compound is 2-(2-n-Propoxyphenyl)-8-(5-phenyl-2-pentyl)-quinazolin-4(3H)-one of the formula

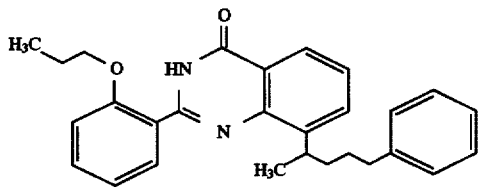

and tautomers and salts thereof.

5. 2,8-disubstituted quinazolinones according to claim 1 wherein such compound is 2-(2-n-Propoxyphenyl)-8-(5-phenyl-3-pentyl)-quinazolin-4(3H)-one of the formula

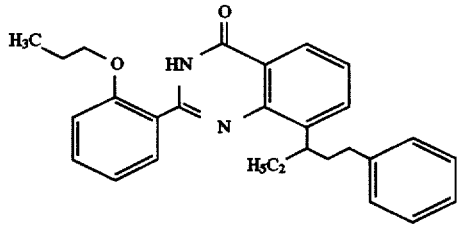

and tautomers and salts thereof.

6. 2,8-disubstituted quinazolinone according to claim 1 wherein such compound is 2-(2-n-Propoxyphenyl)-8-(4-pentyl-1-methoxy-2-hydroxy-1-butyl)-quinazolin-4(3H)-one of the formula

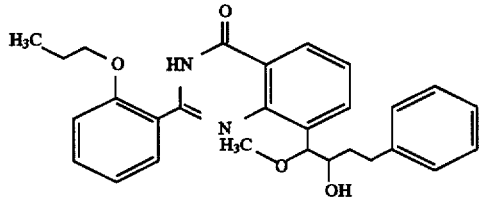

and tautomers and salts thereof.

7. 2,8-disubstituted quinazolinone according to claim 1 wherein such compound is 2-(2-n-Propoxyphenyl)-8-(5-phenyl-3-hydroxy-2-pentyl)-quinazolin-4(3H)-one of the formula

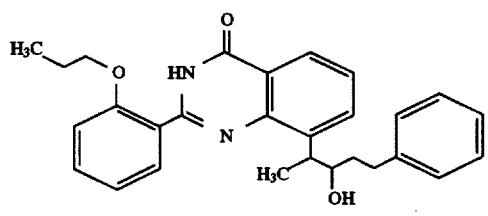

and tautomers and salts thereof.

8. 2,8-disubstituted quinazolinone according to claim 1 wherein such compound is 2-(2-n-Propoxy-5-morpholinosulphonylphenyl)-8-(5-phenyl-2-pentyl)-quinazolin-4-(3H)-one of the formula

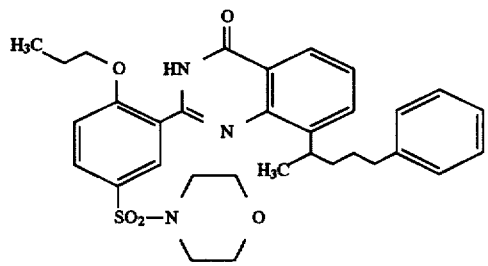

and tautomers and salts thereof.

9. 2,8-disubstituted quinazolinone according to claim 1 wherein such compound is 2-(2-n-Propoxy-5-morpholiphosulphonylphenyl)-8-(5-phenyl-3-pentyl)-quinazolin-4-(3H)-one of the formula

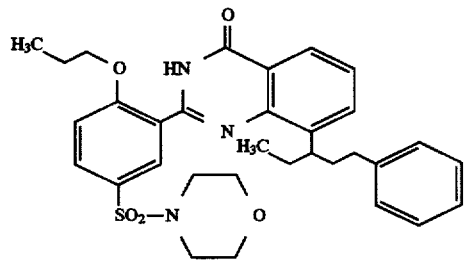

and tautomers and salts thereof.

10. A composition for the treatment of cardiovascular diseases comprising an amount effective therefor of the compound or a tautomer or a salt thereof according to claim 1 and a pharmacologically acceptable diluent.

11. A composition for the treatment of disease of the urogenital system comprising an amount effective therefor of the compound or a tautomer or a salt thereof according to claim 1 and a pharmacologically acceptable diluent.

12. A composition for the treatment of impotence comprising an amount effective therefor of the compound or a tautomer or a salt thereof according to claim 1 and a pharmacologically acceptable diluent.

13. A method of treating cardiovascular diseases in a patient in need thereof which comprises administering to such patient an amount effective therefor of a compound or tautomer or salt thereof according to claim 1.

14. A method of treating diseases of the urogenital system in a patient in need thereof which comprises administering to such patient an amount effective therefor of a compound or tautomer or salt thereof according to claim 1.

15. A method of treating impotence in a patient in need thereof which comprises administering to such patient an amount effective therefor of a compound or tautomer or salt thereof according to claim 1.

16. 2,8-Disubstituted quinazolinones of the general formula (I)

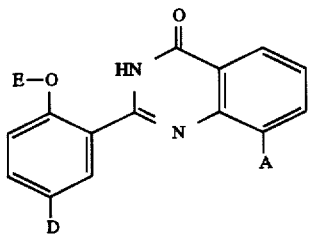

in which

A represents oxiranyl, which is optionally substituted by straight-chain or branched alkyl having up to 8 carbon atoms, which in turn can be substituted by phenyl, or represents a radical of the formula

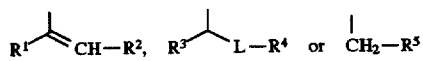

wherein $R^1$ denotes hydrogen or straight-chain or branched alkyl having up to 6 carbon atoms, $R^2$ denotes straight-chain or branched alkyl having up to 8 carbon atoms, which is optionally substituted by phenyl, $R^3$ denotes straight-chain or branched alkyl having up to 5 carbon atoms or a group of the formula —$OR^6$, wherein $R^6$ denotes hydrogen, a hydroxyl-protecting group or straight-chain or branched alkyl having up to 5 carbon atoms, $R^4$ denotes straight-chain or branched alkyl having 2 to 10 carbon atoms, which is optionally substituted by phenyl, L denotes a radical of the formula —CO—, —CH(OH), —$CH_2$, —$CH(N_3)$ or —$CH(OSO_2R^7)$, wherein $R^7$ denotes straight-chain or branched alkyl having up to 4 carbon atoms or phenyl, $R^5$ denotes branched alkyl having 4 to 8 carbon atoms, or denotes straight-chain or branched alkyl having 3 to 8 carbon atoms which is substituted by phenyl, or denotes benzyl or 2-phenylethyl, D represents hydrogen, or represents a group of the formula —$SO_2$—$NR^8R^9$, which $R^8$ and $R^9$ are identical or different and denote hydrogen, phenyl or straight-chain or branched alkyl having up to 6 carbon atoms, which is optionally substituted by hydroxyl, or, together with the nitrogen atom, form a 5- to 6-membered saturated heterocyclic radical which has up to 2 further hetero atoms for the series consisting of S, N and/or O and is optionally substituted, including via a free N function, by straight-chain or branched alkyl having up to 6 carbon atoms, which in turn can be substituted by hydroxyl, and E represents straight-chain or branched alkyl having up to 8 carbon atoms, and tautomers and salts thereof.

* * * * *

UNITED STATES PATENT AND TRADEMARK OFFICE
CERTIFICATE OF CORRECTION

PATENT NO. : 5,721,238

DATED : February 24, 1998

INVENTOR(S) : Fred Robert Heiker et al

It is certified that error appears in the above-identified patent and that said Letters Patent is hereby corrected as shown below:

Column 28, Claim 16, Line 17  Delete "which" and insert --wherein--

Signed and Sealed this

Seventh Day of September, 1999

Attest:

Q. TODD DICKINSON

*Attesting Officer*  Acting Commissioner of Patents and Trademarks